US00PP29329P3

(12) United States Plant Patent
Noodelijk

(10) Patent No.: US PP29,329 P3
(45) Date of Patent: May 29, 2018

(54) ***CELOSIA* PLANT NAMED 'SPITENZ DARK'**

(50) Latin Name: *Celosia argentea*
Varietal Denomination: Spitenz Dark

(71) Applicant: Robert Noodelijk, Woubrugge (NL)

(72) Inventor: Robert Noodelijk, Woubrugge (NL)

(73) Assignee: Floritec Breeding BV (NL)

( * ) Notice: Subject to any disclaimer, the term of this patent is extended or adjusted under 35 U.S.C. 154(b) by 40 days.

(21) Appl. No.: 14/999,490

(22) Filed: May 12, 2016

(65) Prior Publication Data

US 2016/0353634 P1 Dec. 1, 2016

(30) Foreign Application Priority Data

May 26, 2015 (QZ) ..... PBR 2015/1066

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Cassandra Bright

(57) ABSTRACT

A *Celosia* plant named 'Spitenz Dark' characterized by its many dark purple colored spikes, prolific branching, foliage from the bottom to the top of the plant, a compact and symmetrical plant habit, and a response time of approximately 7.5 weeks is disclosed.

3 Drawing Sheets

Genus and species: *Celosia argentea.*
Variety denomination: 'Spitenz Dark'.

BACKGROUND OF THE NEW PLANT

The present invention comprises a new and distinct variety of *Celosia* plant, botanically known as *Celosia argentea*, and hereinafter referred to by the variety name 'Spitenz Dark'. This new variety produces many medium sized spikes with dark purple colored individual blooms and a blooming period of about eight weeks.

The new variety 'Spitenz Dark' is a naturally occurring sport from the unpatented *Celosia* variety 'Innovo'. The new and distinct variety was discovered and selected as a single plant in a greenhouse in Monster, The Netherlands in May 2013.

The new variety 'Spitenz Dark' was first asexually reproduced by terminal vegetative cuttings in a greenhouse in Monster, The Netherlands in August 2013 and has been asexually reproduced for one and a half years. The new variety 'Spitenz Dark' has been found to retain its distinctive characteristics through successive asexual propagations.

SUMMARY OF THE INVENTION

The following are the most outstanding and distinguishing characteristics of the new variety when grown under normal horticultural practices in Monster, The Netherlands.

1. Dark purple spiked-type inflorescences having an abundance of spikes on each branch;
2. Prolific branching;
3. Compact symmetrical plant habit; and
4. Foliage located all over the stem to the bottom of the plant.

COMPARISON WITH THE PARENT VARIETY

The new variety 'Spitenz Dark' differs from parent variety in having a darker flower color.

COMPARISON WITH COMMERCIAL VARIETIES

The new variety 'Spitenz Dark' differs from the commercial *Celosia* 'Spitenz' U.S. Plant Pat. No. 23,076 in that 'Spitenz Dark' is a more compact plant. Further, the new variety 'Spitenz Dark' has a darker flower color and has broader and shorter spikes than 'Spitenz'. The new variety 'Spitenz Dark' has foliage that is narrower and slightly smaller than that of 'Spitenz' and a flowering response time that is approximately one week longer than the response time of 'Spitenz'.

The new variety 'Spitenz Dark' can also be compared to *Celosia* 'Spitenz Lipstick' patent pending, filed concurrently having application Ser. No. 14/999,491. 'Spitenz Dark' produces darker colored flowers. Further, the new variety 'Spitenz Dark' has shorter flowering spikes on average than 'Spitenz Lipstick'. The new variety 'Spitenz Dark' produces less flowering spikes per plant than 'Spitenz Lipstick'. Peduncles and stems of 'Spitenz Dark' are colored near yellow-Green 146C, compared to Red-Purple 58A appearing on 'Spitenz Lipstick'.

DESCRIPTION OF THE PHOTOGRAPHS

This new *Celosia* plant is illustrated by the accompanying photographs which show blooms and foliage of the plant. The colors shown are as true as can be reasonably obtained by conventional photographic procedures. The photographs are of a plant that has been in bloom for approximately 3 weeks.

DESCRIPTION OF THE NEW VARIETY

Figure 1:
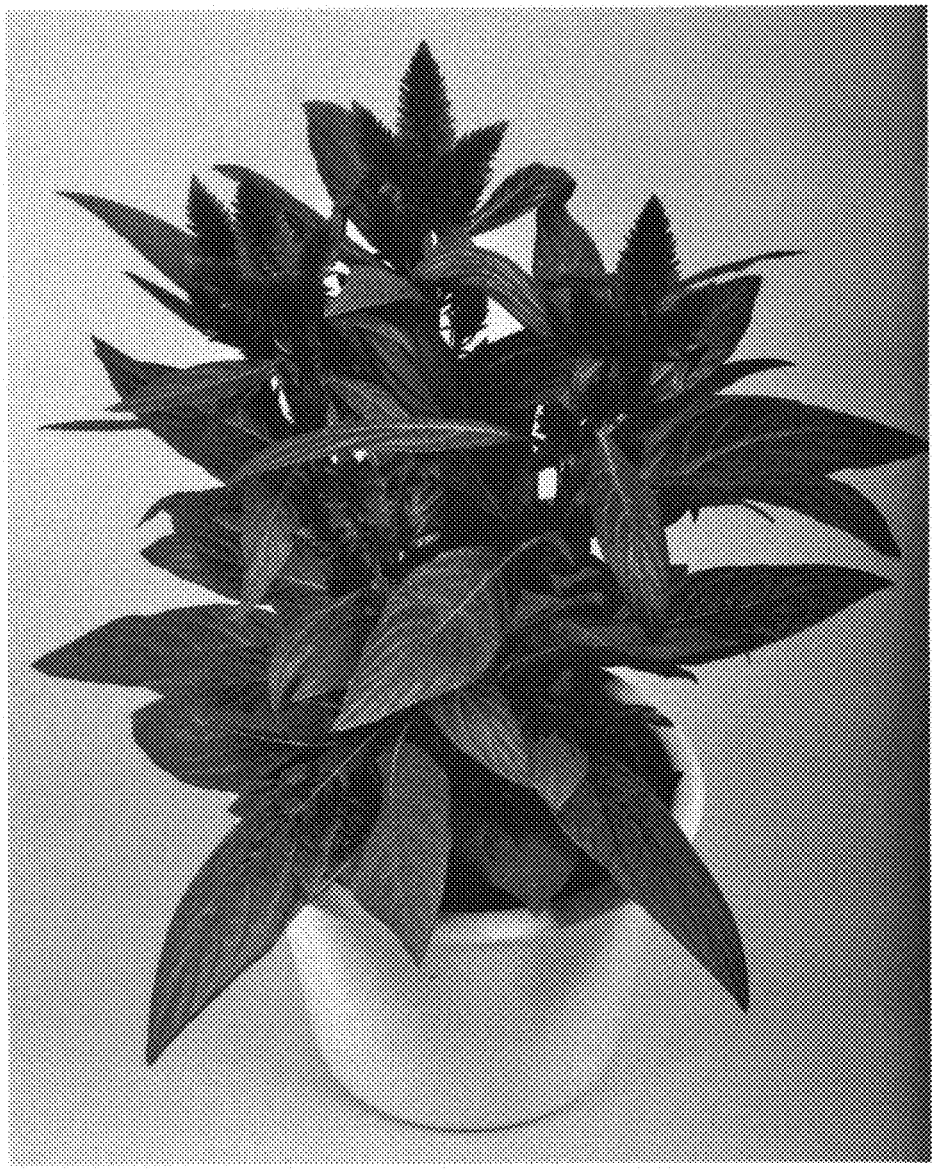
FIG. 1 shows the plant habit including the foliage and inflorescences of the new variety.
Figure 2:
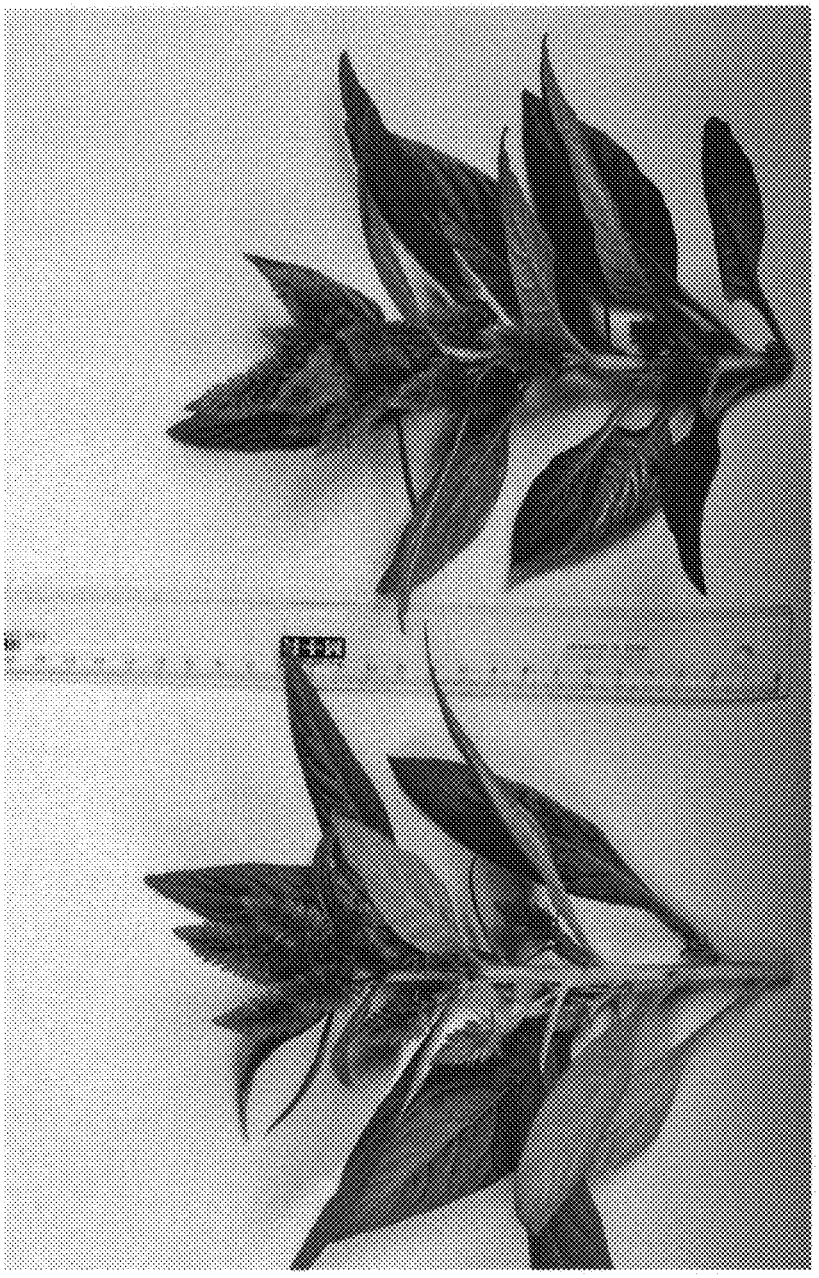
FIG. 2 is a close-up of the new variety 'Spitenz Dark', showing individual spikes and inflorescences per branch.
Figure 3:
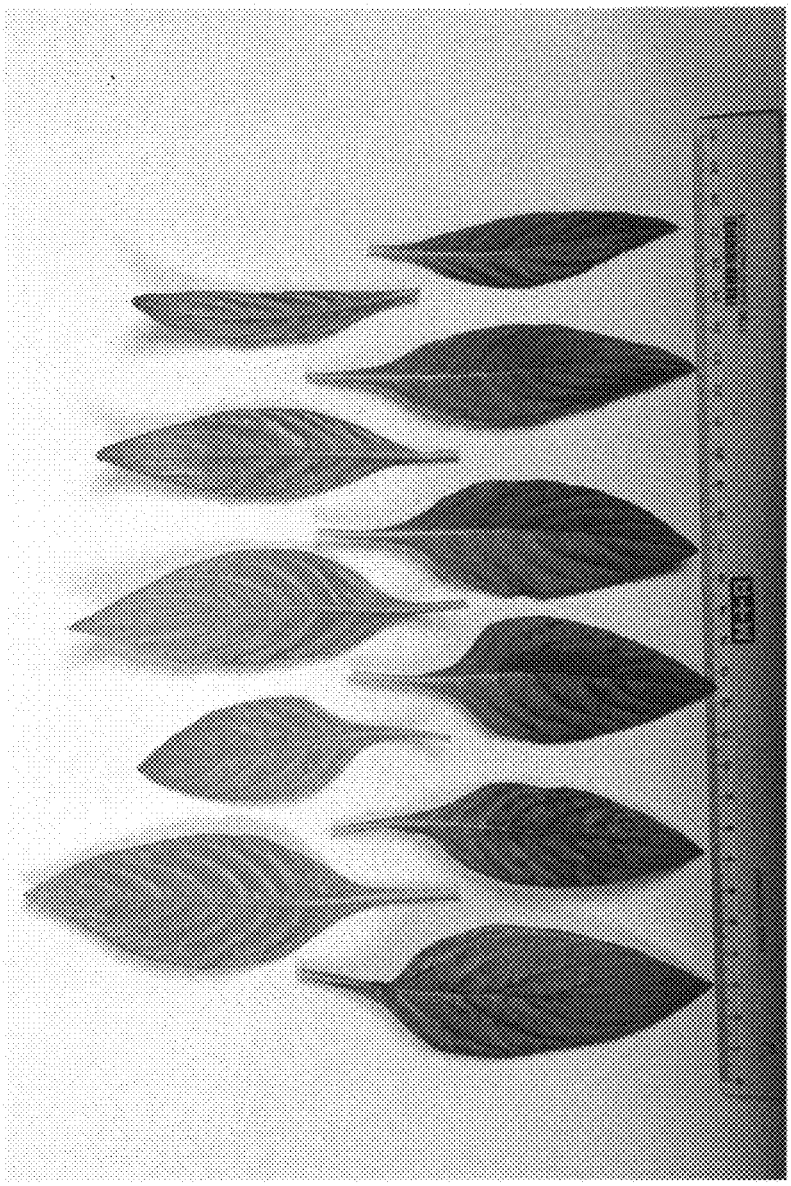
FIG. 3 is a close-up of the upper and under surfaces of the leaves of the new variety 'Spitenz Dark'.

The following detailed descriptions set forth the distinctive characteristics of 'Spitenz Dark'. The data which define these characteristics were collected from asexual reproductions carried out in Monster, The Netherlands. The plant history was taken on un-pinched plants of 8 to 10 weeks old, which were grown in 10 cm pots in a greenhouse in Monster, The Netherlands under controlled day length and temperatures. Growth retardants were used weekly. The color readings were determined under natural light. Color references are to The R.H.S. Colour Chart of The Royal Horticultural Society of London (R.H.S.), 1995 Edition.

DETAILED BOTANICAL DESCRIPTION

Classification:
- *Botanical.*—*Celosia argentea.*
- *Common name.*—Cockscomb, Woolflower, Feathery Amaranth.
- *Denomination.*—'Spitenz Dark'.

Plant:
- *Growth habit.*—Upright, slightly upwardly spreading annual.
- *Growth rate.*—Rapid.
- *Height.*—28.0 to 32.0 cm (using weekly growth retardant).
- *Width.*—20.0 to 25.0 cm (using weekly growth retardant).

Branches:
- *Stem.*—Color: RHS 146C (Green). Strength: Strong. Brittleness: Branches are not brittle. Cross section: Round. Texture: Smooth, no significant ribs.

Anthocyanin coloration: Present at nodes, near RHS Red-Purple 59A.
- *Length of lateral branch* (*from top to bottom*).—13.0 cm to 20.0 cm.
- *Diameter of lateral branch.*—0.5 cm.
- *Lateral branch color.*—RHS 146C (Green).
- *Lateral branch attachment.*—Petiolate.
- *Branching.*—Average number of lateral branches: Prolific, with 4 to 8 breaks after pinching.

Leaves:
- *Type.*—Single, simple.
- *Arrangement.*—Alternate.
- *Color.*—Upper surface: RHS 137A (Green and partially turning RHS 59A (Red-Purple) with age). Lower surface: RHS 147B (Green). Veins: RHS 45B (Red).
- *Size.*—General: Medium.
- *Immature foliage.*—Length: 9.5 cm. Width: 1.5 cm.
- *Mature foliage.*—Length: 14.0 cm. Width: 4.0 cm.
- *Quantity per lateral branch.*—12 to 16.
- *Shape.*—Cordiform.
- *Apex.*—Acuminate.
- *Base.*—Attenuate.
- *Margin.*—Entire.
- *Texture.*—Upper surface: Leathery. Lower surface: Leathery.
- *Petiole.*—
- *Color.*—Near Yellow-Green 146A flushed with anthocyanin near Red-Purple 59A.
- *Length.*—0.5 cm.
- *Width.*—0.1 cm.
- *Venation arrangement.*—Pinnate.

Inflorescence:
- *Type.*—Many small individual tubular flowers on a spiked-type inflorescence.
- *Height.*—1 week old spike: 2.5 to 3.5 cm. 3 week old spike: 4.0 to 5.0 cm.
- *Width.*—Mature spike approximately 1.5 to 2 cm at widest point.
- *Number of spikes per branch.*—Approximately 11 per branch.
- *Number of flowers per spike.*—1 week old spike: Approximately 65 to 75. 3 week old spike: Approximately 90 to 110.
- *Inflorescence lastingness on the plant* (*blooming period*).—8 weeks.
- *Fragrance.*—Absent.
- *Discoloration to color.*—None.
- *Peduncle.*—Length: 1.0 cm to 2.0 cm. Diameter: 0.3 cm. Color: RHS 146C (green).
- *Response time.*—7.5 weeks.

Florets:
- *Number of petals per floret.*—5.
- *Petal texture* (*both surfaces*).—Papery, glabrous.
- *Apex.*—Acuminate.
- *Margin.*—Entire.
- *Length.*—0.5 cm.
- *Width.*—0.1 cm.
- *Color.*—(Both surfaces): RHS 72A (Red-Purple).

Floral bracts: Not Present.

Reproductive organs:
- *Stamen.*—Width: Very thin, 0.05 cm. Color: RHS 72A (Red-Purple). Pollen amount: Sparse; appears at a very late stage. Pollen color: RHS 155A (White).
- *Pistil.*—Style appearance: Very fine, linear. Style color: RHS 72A (Red-Purple). Style length: 0.6 cm. Stigma color: RHS 72A (Red-Purple). Stigma width: 0.1 cm.

Other characteristics:

Fruit/seed set: Not observed.

Disease/pest resistance: Typical to known *Celosia* varieties. Neither resistance nor susceptibility to the normal diseases and pests of *Celosia* have been observed. Pests common to *Celosia* include Aphids and thrips. Typical diseases are *Botrytis* and *Pythium.*

Temperature tolerance: 5° C. to 38° C.

Drought tolerance: No tolerance for drought.

What is claimed is:

1. A new and distinct variety of *Celosia* plant named 'Spitenz Dark' as described and shown herein.

* * * * *